United States Patent
Allef et al.

(10) Patent No.: US 7,163,916 B2
(45) Date of Patent: Jan. 16, 2007

(54) PROCESS FOR THE PREPARATION OF HIGHLY CONCENTRATED FLOWABLE AQUEOUS SOLUTIONS OF BETAINES

(75) Inventors: Petra Allef, Bonn (DE); Uwe Begoihn, Essen (DE); Burghard Grüning, Essen (DE); Ralf Klein, Velbert (DE); Jörg Peggau, Essen (DE)

(73) Assignee: Goldschmidt GmbH, Essen (DE)

( * ) Notice: Subject to any disclaimer, the term of this patent is extended or adjusted under 35 U.S.C. 154(b) by 0 days.

(21) Appl. No.: 11/281,825

(22) Filed: Nov. 17, 2005

(65) Prior Publication Data

US 2006/0128599 A1    Jun. 15, 2006

(30) Foreign Application Priority Data

Nov. 17, 2004    (DE) .............. 10 2004 055 549

(51) Int. Cl.
  *C11D 3/00*    (2006.01)
  *C11D 3/37*    (2006.01)
  *C11D 17/00*   (2006.01)
  *C11D 17/08*   (2006.01)

(52) U.S. Cl. ............... 510/433; 510/340; 510/350; 510/504

(58) Field of Classification Search ........... 510/123, 510/124, 155, 326, 340, 350, 356, 433, 475, 510/476, 499, 504
See application file for complete search history.

(56) References Cited

U.S. PATENT DOCUMENTS

| | | | | |
|---|---|---|---|---|
| 4,832,871 A | * | 5/1989 | Bade | 516/69 |
| 5,354,906 A | * | 10/1994 | Weitemeyer et al. | 554/52 |
| 6,191,083 B1 | * | 2/2001 | Brooks et al. | 510/124 |
| 6,218,345 B1 | * | 4/2001 | Brooks et al. | 510/123 |
| 6,525,034 B1 | * | 2/2003 | Dalrymple et al. | 514/77 |
| 6,683,033 B1 | | 1/2004 | Gonzalez et al. | |

FOREIGN PATENT DOCUMENTS

| | | |
|---|---|---|
| DE | 36 13 944 C1 | 8/1987 |
| DE | 42 07 386 C2 | 8/1993 |
| EP | 1 140 798 B1 | 10/2001 |
| WO | WO 95/14076 | 5/1995 |
| WO | WO 01/30744 * | 5/2001 |

* cited by examiner

*Primary Examiner*—Douglas McGinty
*Assistant Examiner*—John M. Petruncio
(74) *Attorney, Agent, or Firm*—Scully, Scott, Murphy & Presser, P.C.

(57) ABSTRACT

The invention relates to a process for preparing highly concentrated flowable and pumpable aqueous solutions of betaines by quaternization of compounds containing tertiary amine nitrogen with ω-halocarboxylic acids by known processes, wherein 0.1 to less than 3% by weight, preferably 0.1 to 1% by weight, based on the end product, of one or more micellar thickeners are added to the reaction mixture before or during the quaternization reaction.

6 Claims, No Drawings

PROCESS FOR THE PREPARATION OF HIGHLY CONCENTRATED FLOWABLE AQUEOUS SOLUTIONS OF BETAINES

FIELD OF THE INVENTION

The present invention relates to a process for the preparation of highly concentrated flowable aqueous solutions of betaines with betaine contents of up to about 55% by weight.

BACKGROUND OF THE INVENTION

Betaines have established themselves in recent years in the cosmetic industry as a firm constituent of formulations, in particular, for cleansing the hair and body. Betaines are able to form a dense and creamy lather which remains stable over a long period even in the presence of other surfactants, soaps and additives. Moreover, betaines have recognized good cleaning properties without any irritative side-effects, even for sensitive skin.

The preparation of betaines is described in detail in the relevant patent and specialist literature (see, for example, U.S. Pat. No. 3,225,074). In general, compounds containing tertiary amine nitrogen atoms are reacted with ω-halocarboxylic acids or salts thereof in aqueous or hydrous media.

The compounds containing tertiary amine nitrogen atoms used are, in particular, fatty acid amides of the general formula (I)

$$R^3\text{—CONH—}(CH_2)_m\text{—}NR^4R^5 \quad (I)$$

in which
R$^3$ is an alkyl radical of a fatty acid which is optionally branched and can optionally comprise multiple bonds, optionally hydroxyl groups,
R$^4$, R$^5$ are identical or different alkyl radicals having 1 to 4 carbon atoms, and
m may be 1 to 3.

The alkyl radical R$^3$ can be derived from natural or synthetic fatty acids having 6 to 20 carbon atoms, preferably from natural vegetable or animal fatty acids having 8 to 18 carbon atoms, and their naturally occurring or specifically adapted mixtures with one another or among one another.

Suitable fatty acids are, for example, caproic acid, caprylic acid, capric acid, lauric acid, palmitic acid, stearic acid, behenic acid, linoleic acid, linolenic acid, and ricinoleic acid.

Preference is given to the naturally occurring fatty acid mixtures with a chain length of from 8 to 18 carbon atoms, such as coconut fatty acid or palm kernel fatty acid, which can optionally be hydrogenated by suitable hydrogenation methods.

These fatty acids and fatty acid mixtures are reacted by customary condensation reaction in a first process stage at 140° to 200° C. with amines of the general formula (II)

$$H_2N\text{—}(CH_2)_m\text{—}NR^4R^5 \quad (II)$$

in which R$^4$ and R$^5$ and m have the meaning specified in the formula (I), to give the fatty acid amides with tertiary nitrogen atoms of the general formula (I).

The subsequent quaternization reaction to give betaines of the formula (III)

$$R^3\text{—CONH—}(CH_2)_m\text{—}N^+R^4R^5(CH_2)_y COO^- \quad (III)$$

in which R$^3$, R$^4$, R$^5$ and m have the same meaning as in the formulae (I) and (II) and y may be 1, 2 or 3, is carried out according to the process known in the literature as the second process stage.

The process usually involves adding ω-haloalkylcarboxylic acids, preferably chloroacetic acid or the sodium salt of chloroacetic acid to the fatty acid amide of the formula (I) in the aqueous medium and completing the quaternization in a reaction for several hours at about 80° to 100° C. Depending on the fatty acid or fatty acid mixture used, in order to maintain stirrability, a minimum amount of water must be present as the reaction progresses. The standard commercial solids concentration of the betaine solutions prepared in this way is therefore about 35 to 37% by weight or below.

However, to reduce storage and transportation costs and for formulation-related reasons during further processing, in many cases a higher concentration is strongly desired. In the past, a series of processes to fulfill this requirement have therefore been proposed. The solids content of these mostly highly viscous solutions could, however, only be increased to about 50%, and in the case of commercial highly concentrated betaines, it is mostly about 45%, the active betaine content thus being about 35%.

DE-C-3 613 944 discloses a process in which the quaternization is carried out in an organic polar solvent with a water fraction of 20% by weight and some, or all, of the solvent is removed by distillation and then the desired concentration is established again using an industrially usable solvent. Apart from the fact that the process is technically complex and cost-intensive, organic solvents and also the residual contents, which cannot be removed by distillation during further processing, are often undesired in cosmetic formulations.

Although the process according to DE-C-3 826 654 contains an example without an organic solvent, the viscosities obtained are too high for industrial production. Furthermore, relatively large amounts (3 to 20% by weight) of a nonionic surfactant (polyoxyethylene ether with 10 to 250 oxyethylene units) are required as a liquefier. Added amounts, in this order of magnitude, are undesired since they can adversely affect the end formulations in physical and/or physiological terms.

DE-C-4 207 386 describes highly concentrated betaines which comprise 1 to 3% by weight of saturated or unsaturated fatty acid as a thinning principle. Betaines which are prepared by this method can be concentrated up to a solids content of 48% by weight.

Similar concentrations are obtained according to EP-B-1 140 798. The thinning principles here are glutamic acid (salts) and analogous amino acids, which are added to the quaternization reaction.

DE-C-19 505 196 describes the use of sulfobetaines, amphoglycinates, trimethylglycine or dicarboxylic acid (diamides) in concentrations of from 4 to 8% by weight during the carboxymethylation. The betaines obtained have a solids content of about 50% by weight and an average viscosity.

The solids content is likewise 50% by weight for betaines which have been prepared according to DE-A-19 700 798 using up to 5% by weight of polybasic optionally hydroxy-functionalized carboxylic acids during the carboxymethylation.

Similar solids contents are achieved by adding 0.05 to 2% by weight of cyclodextrins or dextrans, as described in DE-A-10 207 924.

The use of 0.5 to 5% by weight, preferably 2 to 4% by weight, of betaines from short-chain mono- or dicarboxylic acids for diluting cocobetaine is described in EP-C-656 346. Here, betaines with a solids concentration of 45% by weight are obtained.

DE-C-4 408 183 describes betaines with up to 54% by weight of solids. The betaines comprise 1 to 10% by weight of a hydroxycarboxylic acid. In order to obtain flowable products with more than 50% by weight of solids, about 5% by weight of citric acid is required. The betaine content is then about 32% by weight.

DE-C-19 523 477 describes the use of polyfunctional carboxamides, e.g., adipic acid diamidamine, during carboxymethylation. Although the described betaine concentrates comprise 60% by weight of solids, the betaines are no longer of low viscosity. Since during the carboxymethylation a viscosity maximum is passed through, industrial preparation of these products is very costly and complicated unless large amounts of adipic acid betaine are added to the betaine, which, in turn, strongly influences the properties of the betaine.

Solids contents of about 50% by weight are also obtained according to U.S. Pat. No. 6,683,033. Here, 0.5 to 3.5% by weight of phosphoric esters of optionally low-ethoxylated fatty alcohols and/or dimer acids are used as liquefiers. The betaine content of the examples is below 37%.

DE-C-4 408 228 describes betaines with solids contents above 50% by weight comprising 1 to 10% by weight of a nonionic surfactant with HLB 6 to 12 and/or hydroxycarboxylic acids, 1 to 6% by weight of polyols and optionally 1 to 10% by weight of fatty acid (salts). For high solids contents, in most cases greater than 6% by weight of additives are required, which is undesirable with regard to potentially negative effects on formulations. The actual betaine content is only about 32% by weight.

Due to the high storage and transportation costs relative to the price of the product, there is a need for even more highly concentrated flowable and pumpable aqueous solutions of betaines which are free from lower alcohols such as, for example, methanol, ethanol, propanol or isopropanol.

SUMMARY OF THE INVENTION

The present invention provides a process for the preparation of a flowable and pumpable betaine concentrate with which significantly higher solids/active substance contents can be achieved than with the known processes. Moreover, the present invention provides a process where the reaction mixtures are easy to handle and not too highly viscous during the entire production process. Furthermore, the present invention provides a method where the reaction products do not after-thicken or gel upon subsequent storage.

It is known in the literature (e.g., EP-A-679 180 and references therein) that in the conventional preparation of surfactant concentrates, spherical micelles form first, which then convert to rod-like micelles. This state is generally referred to as $M_1$ phase.

In surfactant mixtures with a higher concentration, liquid-crystalline structures, so-called lamellar phases or G phases, can form. These are mostly formed in a narrow range between 40 and 85% by weight solids content. The G phase is a pumpable liquid in which the surfactant molecules arrange themselves in layers, so-called lamellar layers.

In EP-A-679 180, for the preparation of such G phases, 5 to 45% by weight of a non-water-miscible organic solvent are used, in DE-A-2 921 366, 5 to 45% by weight of a nonionic surfactant with an HLB value in the range 6 to 12 are used.

Surprisingly, it has now been found that flowable and pumpable betaine solutions with betaine contents of greater than about 32% by weight and, in particular, 35% by weight, and up to about 55% by weight and higher, can be prepared from the reaction mixture of fatty acid amide and ω-haloalkylcarboxylic acid by known processes if small amounts of from 0.1 to <3% by weight, preferably 0.1 to 2% by weight, in particular 0.3 to 1% by weight, based on the end product, of one or more micellar thickeners, preferably one or more nonionic, preferably highly ethoxylated surfactants, are added before or during the quaternization reaction.

The solids contents, consisting of the betaine content and the content of further nonvolatile reaction by-products are in the range from about 40 to about 70% by weight, depending on the particular preparation process (reaction parameters, molar ratios) and possible additional components.

These added surfactants effectively prevent, completely or partially, the increase in viscosity which arises during the quaternization and thus permit the preparation of highly concentrated, gel-free betaine solutions which are flowable and pumpable due to the likewise reduced viscosity of the end products.

The invention therefore provides a process for the preparation of highly concentrated flowable and pumpable aqueous solutions of betaines of the general formula (III)

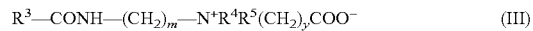

$$R^3\text{—CONH—}(CH_2)_m\text{—}N^+R^4R^5(CH_2)_y COO^- \qquad (III)$$

in which $R^3$ is an alkyl radical of a fatty acid which is optionally branched, can optionally comprise multiple bonds, optionally hydroxyl groups, $R^4$, $R^5$ are identical or different alkyl radicals having 1 to 4 carbon atoms, m may be 1 to 3 and y may be 1, 2, 3, with a betaine content of at least 32% by weight, preferably at least 35% by weight, by quaternization of compounds containing tertiary amine nitrogen with ω-halocarboxylic acids by known processes, wherein 0.1 to less than 3% by weight, preferably 0.1 to 2% by weight, in particular 0.3 to 1% by weight, based on the end product, of one or more micellar thickeners, in particular water-soluble, nonionic surfactants, preferably highly ethoxylated, i.e., with an HLB greater than 12, are added to the reaction mixture before or during the quaternization reaction.

The teaching according to the invention can be applied synergistically to all known dilution principles. In general, up to 20% by weight higher betaine contents are obtained than through the literature-known processes alone. In the case of higher fractions of micellar thickeners, in particular greater than about 1 to 1.5 to less than 3% by weight, these are preferably used in a mixture with one another and/or with the liquefying agents known from the prior art.

DETAILED DESCRIPTION OF THE INVENTION

The invention therefore further provides a process for the preparation of highly concentrated flowable and pumpable aqueous solutions of betaines by quaternization of compounds containing tertiary amine nitrogen with ω-halocarboxylic acids by known processes, wherein, in addition to the micellar thickeners, at least one compound chosen from the group of sulfobetaines, amphoglycinates, trimethylglycines, amino acids, monocarboxamides, monocarboxamidoamines, di-/polycarboxylic acid mono- and/or diamides, monobasic, optionally hydroxy-functionalized carboxylic acids, di-/polyfunctional, optionally hydroxy-functionalized carboxylic acids, water-soluble carbohydrates, polyols is added to the reaction mixture in the customary literature-known concentrations before, during or after the quaternization reaction.

It was surprising that these small amounts of micellar thickeners have this sharply improved effect in the case of more highly concentrated solutions since, according to the teaching of DE-C-3 826 654, only the addition of relatively large amounts greater than 3% of nonionic surfactants should bring about a viscosity-lowering effect.

It was also surprising to discover that particularly when working without solvents and in the case of solids contents of greater than 45% by weight, the addition of greater than 3% by weight, as described in DE-C-3 826 654, in most cases leads to an opposite effect, i.e., to an increase in the viscosity.

For the purposes of the present invention, micellar thickeners are interface-active compounds which are often used for increasing the viscosity of surfactant-containing formulations; they are usually also referred to as associative thickeners. A distinction can be made between hydrophilic and hydrophobic thickeners.

Suitable micellar thickeners preferably consist of one or more oligomeric or polymeric hydrophilic basic building blocks, preferably chosen from the product groups of polyalkylene oxides, polyglycidol, polyglycerol or polyamines linked to long-chain lipophilic alkyl radicals.

Suitable hydrophilic micellar thickeners are addition products of alkylene oxides onto suitable starter molecules such as water, alcohols, acids, amines with optionally esterified or etherified end-groups.

The alkylene oxides used are, in particular, ethylene oxide or propylene oxide for forming homopolymers or polymers with random or blockwise distribution. These polymers can also be prepared by addition of alkylene oxides onto preferably low molecular weight mono- or polyfunctional alcohols or amines, such as methanol, ethanol, butanol, pentanol and higher homologs thereof, ethylene and polyethylene glycols, propylene and polypropylene glycols and higher homologs thereof, glycerol, polyglycerols, sugar alcohols, mono/dialkylethanolamines, mono/diisopropanolamines, polyamines, such as, in particular, alkyl-substituted diaminoethane, diaminopropane, diethylenetriamine, triethylenetetramine and the respective higher homologs.

The long-chain lipophilic alkyl radicals are derived from carboxylic acids, preferably fatty acids, fatty alcohols or fatty amines. The hydrophilic and lipophilic basic building blocks can be linked, for example, by esterification reactions or ether formation, such as, addition onto fatty acids, alcohols or amines.

Suitable acids are mono- or polybasic monomeric or polymeric organic acids, such as, the homologous series of mono-dicarboxylic acids, in particular, for example, palmitic acid, stearic acid, oleic acid, ricinoleic acid, hydroxystearic acid, adipic acid, sebacic acid, azelaic acid, and dimeric fatty acid.

Amines which can be used are mono- or polyfunctional, monomeric or polymeric compounds, such as, for example, the homologous series of alkanamines, such as, in particular, laurylamine, and stearylamine.

Suitable examples of micellar thickeners are, in particular, PEG-200 hydrogenated glyceryl palmate, PEG-80 glyceryl cocoate, PEG-55 propylene glycol dioleate, PEG-120 methylglucose dioleate, PEG-200 hydrogenated glyceryl cocoate, PEG-200 hydrogenated castor oil, PEG-30 glyceryl cocoate, and block copolymers of alcohols which are also known under the name Pluronic grades and also Pluriol grades.

Further examples are PEG-150 distearate, PEG-100 stearate, and PEG-40 stearate.

Suitable amine-started compounds are ethylenediamine block polymers, alkoxylated amines and polyamines.

Further nonpolymeric, more hydrophobic micellar thickeners can, for example, have the following structures: cocamide DEA (amide of coconut fatty acid or diethanolamine), oleamide DEA, isostearamide MIPA (=methylisopropanolamine), glyceryl laurate, glyceryl oleate, polyglyceryl-3 caprate, laureth-4, palmamidopropyltrimonium chloride, and bis(oleylcarboxyethyl)hydroxyethylmethylammonium methosulfate.

For the systems according to the invention, the structures of the hydrophilic thickeners with a molecular weight greater than 1500 g/mol, preferably greater than 3000 g/mol to about 15000 g/mol, exhibit the best effects, i.e., in low concentrations they effectively prevent the formation of a viscous phase and thus clearly improve the flow behavior of highly concentrated surfactant systems.

The addition according to the invention of the micellar thickeners improves the betaine solution many times over with regard to its processing properties: the betaine solutions are surprisingly of low viscosity, meaning that, even in highly concentrated formulations, the content of solvents such as ethanol can be noticeably reduced or avoided altogether; they can be more easily diluted with water, are stable at low temperatures and do not become cloudy even at −15° C.

It is advantageous for the process according to the invention if the amidation of the first stage is carried out in the presence of at least one mono- or polybasic carboxylic acid optionally containing multiple bonds and/or OH groups, in particular $C_{1-5}$-monocarboxylic acids such as formic acid, acetic acid, lactic acid, acrylic acid, methacrylic acid, sorbic acid and/or $C_{2-10}$-di-/polycarboxylic acids such as oxalic acid, malonic acid, succinic acid, adipic acid, azelaic acid, maleic (fumaric) acid.

The quaternization reaction of compound (I) with chloroacetic acid and alkali metal/alkaline earth metal hydroxide or with the alkali metal/alkaline earth metal salt of chloroacetic acid is carried out by reaction for several hours in an aqueous medium at 80° to 100° C., where 0.1 to less than 3% by weight, preferably 0.1 to 1% by weight, of one or more water-soluble, nonionic surfactants are added as viscosity regulators before or during the quaternization reaction.

The water-soluble, nonionic surfactant co-used is at least one compound selected from the group of polyoxyethylene esters of fatty acids or of polyoxyethylene ethers of optionally partial fatty acid esters of polyhydric alcohols, such as, glycerol, sorbitol or glucose. The polyoxyethylene derivatives may also comprise fractions of polyoxypropylene.

The fatty acids used for preparing these nonionic surfactants are preferably the fatty acids which occur in nature. They may be saturated or unsaturated. Particular preference is given to derivatives of hydroxy fatty acids, ricinoleic acid or hydroxystearic acid, and glycerides thereof, e.g., ricinus oil.

The polyoxyethylene ethers of fatty alcohols are based on fatty alcohols which may be saturated or unsaturated, substituted or unsubstituted. Examples of such fatty alcohols are lauryl alcohol, stearyl alcohol and oleyl alcohol.

Preferably, the HLB value of these nonionic surfactants should be greater than 12. Of particular suitability are polyoxyethylene ethers and esters of hydroxy fatty acids and hydroxy fatty acid glycerides with an average content of from 10 to 250 oxyethylene units.

Without wishing to limit the invention to them, the following examples of the micellar thickeners according to the invention are specified: REWODERM LI 52 (PEG-200 hydrogenated glyceryl palmate), REWODERM LI S 80 and ANTIL 200 (PEG-200 hydrogenated glyceryl palmate), ANTIL 141 (PEG-55 propylene glycol oleate), ANTIL 120 (PEG-120 methylglucose dioleate), Varonic LI 520 (PEG-200 hydrogenated glyceryl cocoate, REWOPAL PEG 6000 DS (PEG-150 distearate), TEGO alkanol S 100 (PEG-100 stearate) and TAGAT R 200 (PEG-200 hydrogenated castor oil).

The process is carried out in accordance with the processes known in the prior art, the essential change being the addition of the nonionic surfactants co-used as micellar thickeners before or during the quaternization reaction. In this connection, all literature-known processes for the preparation of concentrated betaine solutions, e.g., addition of optionally polybasic hydroxycarboxylic acids, of polyols, of amino acids, of short-chain betaines or betaines from dicarboxylic acids, can be used additively. Synergistic effects are observed. Industrially, up to about 20% by weight more highly concentrated betaine solutions are obtainable than in processes which do not use the described nonionic surfactants.

The procedure according to the invention preferably involves neutralizing the initial charge of ω-halocarboxylic acid with at least one alkali metal or alkaline earth metal hydroxide and, during the reaction for several hours in the aqueous medium at 80° to 100° C., maintaining the pH of the solution between 8 and 10 by adding a base, preferably an alkali metal hydroxide, and, after the quaternization, adjusting the pH to pH 4.5 to 6 using an organic or inorganic acid.

The betaine according to the invention can be used for formulating washing and cleaning compositions and in cosmetic formulations, e.g., in shampoos, shower baths and liquid soaps. In formulations, it may be combined with e.g., wetting agents, surfactants and/or emulsifiers selected from the groups of anionic, cationic, zwitterionic, amphoteric and/or nonionic surfactants, such as fatty alcohol sulfates, fatty alcohol ether sulfates, alkylsulfonates, alkylbenzenesulfonates, alkyl sulfosuccinates, alkyl ether sulfosuccinates, quaternary ammonium salts, alkylbetaines, other fatty acid amidoalkylbetaines, derivatives of monomeric or condensed saccharides, such as sugar esters, methyl or ethyl glucoside fatty acid esters, alkyl glucosides, ethoxylated fatty alcohols, fatty acid alkanolamides, ethoxylated fatty acid esters, fatty acids or their alkali metal, ammonium, hydroxyalkylammonium salts (soaps), thickeners, such as kaolin, bentonite, fatty alcohols, starch, polyacrylic acid and derivatives, cellulose derivatives, alginates, Vaseline or paraffin, also opacifiers, such as, e.g., derivatives of glycol esters or alcohols, such as, ethanol, propanol, propylene glycol or glycerol, solubilizers, consistency regulators, buffer systems, perfume oils, dyes, also conditioning and care agents, such as, cationic or other amphoteric polymers, lanolin and derivatives, cholesterol, panthenol, pantothenic acid, betaines, polydimethylsiloxanes and/or derivatives, and with all other customary cosmetic ingredients.

The following examples are provide to illustrate the method of the present invention.

Analysis Methods:

Betaine Content:

The betaine content was determined by means of titration with 0.1 M perchloroacetic acid in 1,4-dioxane. The solvent used for the betaine was a methanol/ethylene glycol monomethyl ether mixture (1:3), and the electrode used was a pH electrode.

Water Content:

The water content was determined as the difference from 100—solids content in %. It can also be determined by means of Karl-Fischer titration.

Solids Content:

The solids content was determined by drying the material at 105° C. to a constant weight.

Sodium Chloride:

The content of chloride was determined potentiometrically against a silver nitrate standard solution. The electrode used was a combined silver chloride electrode.

Glycerol Content:

The glycerol content was determined by means of GC in accordance with a customary method.

Viscosity:

The viscosity was measured at room temperature using a Brookfield viscometer (model LVT) with spindle No. 3 at 30 rpm in a 150 ml sample.

EXAMPLES

Preparation of the Amidoamine A.1:

The amidoamine was prepared in a known manner in accordance with EP-C-656 346 by reacting coconut hard fat and 3-dimethylaminopropylamine (DMAPA). In a 500 ml stirred apparatus with reflux condenser and nitrogen inlet, 230 g of coconut hard fat and, as catalyst, 15 g of formic acid were initially introduced and rendered inert using nitrogen for about 10 minutes. 180 ml of 3-dimethylaminopropylamine were then added with stirring and continued inertization with nitrogen. The reaction mixture was brought to 165° C. and maintained at this temperature for about 4 to 5 h. After this time, excess DMAPA was removed by means of vacuum distillation.

Preparation of Amidoamine A.2:

The amidoamine was prepared in a known manner in accordance with EP-C-656 346 by reacting coconut hard fat and 3-dimethylaminopropylamine.

In a 500 ml stirred apparatus with reflux condenser and nitrogen inlet, 230 g of coconut hard fat and, as catalyst, 20 g of acetic acid were initially introduced and rendered inert using nitrogen for about 10 minutes. 180 ml of 3-dimethylaminopropylamine were then added with stirring and continued inertization with nitrogen. The reaction mixture was brought to 165° C. and maintained at this temperature for about 4 to 5 h. After this time, excess DMAPA was removed by means of vacuum distillation.

Preparation of Amidoamine A.3:

The amidoamine was prepared in a known manner in accordance with EP-C-656 346 by reacting coconut hard fat and 3-dimethylaminopropylamine.

In a 500 ml stirred apparatus with reflux condenser and nitrogen inlet, 230 g of coconut hard fat and, as catalyst, 24.3 g of propionic acid were initially introduced and rendered inert using nitrogen for about 10 minutes 180 ml of 3-dimethylaminopropylamine were then added with stirring and continued inertization with nitrogen. The reaction mixture was brought to 165° C. and maintained at this temperature for about 4 to 5 h. After this time, excess DMAPA was removed by means of vacuum distillation.

Preparation of Amidoamine A.4:

The amidoamine was prepared in a known manner in accordance with EP-C-656 346 by reacting coconut hard fat and 3-dimethylaminopropylamine.

In a 500 ml stirred apparatus with reflux condenser and nitrogen inlet, 230 g of coconut hard fat and, as catalyst, 24 g of methacrylic acid were initially introduced and rendered inert using nitrogen for about 10 minutes. 180 ml of 3-dimethylaminopropylamine were then added with stirring and continued inertization with nitrogen. The reaction mixture was brought to 165° C. and maintained at this temperature for about 4 to 5 h. After this time, excess DMAPA was removed by means of vacuum distillation.

Preparation of Amidoamine A.5:

The amidoamine was prepared in a known manner in accordance with EP-C-656 346 by reacting coconut hard fat and 3-dimethylaminopropylamine.

In a 500 ml stirred apparatus with reflux condenser and nitrogen inlet, 237 g of coconut hard fat and, as catalyst, 13 g of adipic acid were initially introduced and rendered inert using nitrogen for about 10 minutes. 180 ml of 3-dimethylaminopropylamine were then added with stirring and continued inertization with nitrogen. The reaction mixture was brought to 165° C. and maintained at this temperature for about 4 to 5 h. After this time, excess DMAPA was removed by means of vacuum distillation.

Preparation of Amidoamine B:

The amidoamine was prepared according to the prior art (DE-C-4 207 386) by reacting coconut hard fat and 3-dimethylaminopropylamine in the presence of a catalyzing fatty acid.

In a 500 ml stirred apparatus with reflux condenser and nitrogen inlet, 230 g of coconut hard fat and, as catalyst, 2 g of coconut fatty acid were initially introduced and rendered inert with nitrogen for about 10 minutes. 180 ml of 3-dimethylaminopropylamine were then added with stirring and continued inertization with nitrogen. The reaction mixture was brought to 165° C. and maintained at this temperature for about 4 to 5 h. After this time, excess DMAPA was removed by means of vacuum distillation.

Preparation of Amidoamine C:

The amidoamine was prepared according to the prior art by reacting coconut hard fat and 3-dimethylaminopropylamine in the absence of a catalyzing fatty acid.

In a 500 ml stirred apparatus with reflux condenser and nitrogen inlet, 230 g of coconut hard fat were rendered inert using nitrogen for about 10 minutes.

180 ml of 3-dimethylaminopropylamine were then added with stirring and continued inertization with nitrogen. The reaction mixture was brought to 165° C. and maintained at this temperature for about 4 to 5 h. After this time, excess DMAPA was removed by means of vacuum distillation.

Preparation of a Concentrated Aqueous Betaine Solution:

Example 1.1

(According to the Invention)

40 g of Na monochloroacetate and 115.6 g of water were weighed into a 1 l four-necked flask fitted with stirrer, thermometer, reflux condenser and dropping funnel. Following the addition of 1.3 g of polyethoxylated castor oil with 200 oxyethylene units, 100 g of coconut fatty amidopropyldimethylamine, as described in example A.1, were added over a period of 15 minutes. The reaction mixture was then heated to 70° C. and the temperature was maintained until the heat of reaction had passed. The mixture was then heated to 98° C. After about 7 h, the content of amide was below 0.5%. 256 g of an aqueous betaine solution of the following composition were obtained:
Betaine content: 47.2%
Water: 45.0%
Viscosity: 170 mPa·s Example 1.2

(According to the Invention)

40 g of Na monochloroacetate and 115.6 g of water were weighed into a 1 l four-necked flask fitted with stirrer, thermometer, reflux condenser and dropping funnel. Following the addition of 1.3 g of polyethoxylated castor oil with 200 oxyethylene units, 100 g of coconut fatty amidopropyldimethylamine, as described in example A.2, were added over a period of 15 minutes. The reaction mixture was then heated to 70° C. and the temperature was maintained until the heat of reaction had passed. The mixture was then heated to 98° C. After about 7 h, the content of amide was below 0.5%. 256 g of an aqueous betaine solution of the following composition were obtained:
Betaine content: 46.0%
Water: 45.0%
Viscosity: 280 mPa·s Example 1.3

(According to the Invention)

40 g of Na monochloroacetate and 115.6 g of water were weighed into a 1 l four-necked flask fitted with stirrer, thermometer, reflux condenser and dropping funnel. Following the addition of 1.3 g of polyethoxylated castor oil with 200 oxyethylene units, 100 g of coconut fatty amidopropyldimethylamine, as described in example A.3, were added over a period of 15 minutes. The reaction mixture was then heated to 70° C. and the temperature was maintained until the heat of reaction had passed. The mixture was then heated to 98° C. After about 7 h, the content of amide was below 0.5%.

Example 1.4

(According to the Invention)

40 g of Na monochloroacetate and 115.6 g of water were weighed into a 1 l four-necked flask fitted with stirrer, thermometer, reflux condenser and dropping funnel. Following the addition of 1.3 g of polyethoxylated castor oil with 200 oxyethylene units, 100 g of coconut fatty amidopropyldimethylamine, as described in example A.4, were added over a period of 15 minutes. The reaction mixture was then heated to 70° C. and the temperature was maintained until the heat of reaction had passed. The mixture was then heated to 98° C. After about 7 h, the content of amide was below 0.5%. 256 g of an aqueous betaine solution of the following composition were obtained:
Betaine content: 50.3%
Water: 45.0%
Viscosity: 100 mPa·s Example 1.5

(According to the Invention)

40 g of Na monochloroacetate and 116 g of water were weighed into a 1 l four-necked flask fitted with stirrer, thermometer, reflux condenser and dropping funnel. Following the addition of 1.3 g of polyethoxylated castor oil with 200 oxyethylene units, 100 g of coconut fatty amidopropyldimethylamine, as described in example A.5, were added over a period of 15 minutes. The reaction mixture was then heated to 70° C. and the temperature was maintained until the heat of reaction had passed. The mixture was then heated to 98° C. After about 7 h, the content of amide was below 0.5%. 257.3 g of an aqueous betaine solution of the following composition were obtained:
Betaine content: 49.1%
Water: 45.0%
Viscosity: 170 mPa·s

Example 1.6

(According to the Invention)

32.5 g of monochloroacetic acid and 106.8 g of water were weighed into a 1 l four-necked flask fitted with stirrer, thermometer, reflux condenser and dropping funnel. 28.9 g of 50% strength sodium hydroxide were added via the dropping funnel with stirring. The temperature increased during this addition to about 50° C. Over a period of 15 minutes, 100 g of coconut fatty amidopropyldimethylamine, as described in example A.1, with a content of 1.3 of polyethoxylated castor oil having 200 EO units were added. The reaction mixture was then heated to 70° C. and the temperature was maintained until the heat of the reaction had passed. The mixture was then heated to 98° C. After about 7 h, the content of amide was below 0.5%. 269.5 g of an aqueous betaine solution of the following composition were obtained:
Betaine content: 49.0%
Water: 45.0%
Viscosity: 185 mPa·s

Example 1.7

(According to the Invention)

33.2 g of monochloroacetic acid and 85.2 g of water were weighed into a 1 l four-necked flask fitted with stirrer, thermometer, reflux condenser and dropping funnel. 29.6 g of 50% strength sodium hydroxide were added via the dropping funnel with stirring. The temperature increased during this addition to about 50° C. Following the addition of 1.8 g of polyethoxylated castor oil having 200 oxyethylene units, 100 g of coconut fatty amidopropyldimethylamine, as described in example A.1, were added over a period of 15 minutes. The reaction mixture was then heated to 70° C. and the temperature was maintained until the heat of reaction had passed. The mixture was then heated to 98° C. After about 7 h, the content of amide was below 0.5%. 249.8 g of an aqueous betaine solution with 60% solids were obtained which had the following composition:
Betaine content: 49.2%
Water: 40.0%
Viscosity: 180 mPa·s

Example 2.1

(Not in Accordance with the Invention)

38 g of Na monochloroacetate and initially 92 g of water were weighed into a 1 l four-necked flask fitted with stirrer, thermometer, reflux condenser and dropping funnel. Over a period of 15 minutes, 100 g of coconut fatty amidopropyldimethylamine, as described in example A.1, were added. The reaction mixture was then heated to 70° C. and the temperature was maintained until the heat of reaction had passed. Solidification or gelling then took place. The reaction mixture was unstirrable. Through dilution with 76.6 g of water, the reaction mixture was again converted to a stirrable form with difficulty. The mixture was then heated to 98° C. After about 7 h, the content of coconut fatty aminoamide was below 0.5%. 306.7 g of an aqueous betaine solution of the following composition were obtained:
Betaine content: 34.2%
Water: 55.0%
Viscosity: 125 mPa·s

Example 2.2

(Not in Accordance with the Invention)

38 g of Na monochloroacetate and initially 92 g of water were weighed into a 1 l four-necked flask fitted with stirrer, thermometer, reflux condenser and dropping funnel. Over a period of 15 minutes, 100 g of coconut fatty amidopropyldimethylamine, as described in example A.2, were added. The reaction mixture was then heated to 70° C. and the temperature was maintained until the heat of reaction had passed. Solidification or gelling then took place. The reaction mixture was unstirrable. Through dilution with 76.6 g of water, the reaction mixture was again converted to a stirrable form with difficulty. The mixture was then heated to 98° C. After about 7 h, the content of coconut fatty aminoamide was below 0.5%. 306.7 g of an aqueous betaine solution of the following composition were obtained:
Betaine content: 34.3%
Water: 55.0%
Viscosity: 445 mPa·s

Example 2.3

(Not in Accordance with the Invention)

38 g of Na monochloroacetate and initially 92 g of water were weighed into a 1 l four-necked flask fitted with stirrer, thermometer, reflux condenser and dropping funnel. Over a period of 15 minutes, 100 g of coconut fatty amidopropyldimethylamine, as described in example A.3, were added. The reaction mixture was then heated to 70° C. and the temperature was maintained until the heat of reaction had passed. Solidification or gelling then took place. The reaction mixture was unstirrable. Through dilution with 76.6 g of water, the reaction mixture was again converted to a stirrable form with difficulty. The mixture was then heated to 98° C. After about 7 h, the content of coconut fatty aminoamide was below 0.5%. 306.7 g of an aqueous betaine solution of the following composition were obtained:
Betaine content: 34.5%
Water: 55.0%
Viscosity: solid

Example 2.4

(Not in Accordance with the Invention)

38 g of Na monochloroacetate and initially 92 g of water were weighed into a 1 l four-necked flask fitted with stirrer, thermometer, reflux condenser and dropping funnel. Over a period of 15 minutes, 100 g of coconut fatty amidopropyldimethylamine, as described in example A.4, were added. The reaction mixture was then heated to 70° C. and the temperature was maintained until the heat of reaction had passed. Solidification or gelling then took place. The reaction mixture was unstirrable. Through dilution with 76.6 g of water, the reaction mixture was again converted to a stirrable form with difficulty. The mixture was then heated to 98° C. After about 7 h, the content of coconut fatty aminoamide was below 0.5%. 306.8 g of an aqueous betaine solution of the following composition were obtained:
Betaine content: 35.5%
Water: 55.0%
Viscosity: 100 mPa·s

Example 3.1

(According to the Invention)

33.2 g of monochloroacetic acid and 141 g of water were weighed into a 1 l four-necked flask fitted with stirrer, thermometer, reflux condenser and dropping funnel. 29.6 g of 50% strength sodium hydroxide were added via the dropping funnel with stirring. The temperature increased during this addition to about 50° C. Following the addition of 1.8 g of polyethoxylated castor oil having 200 oxyethylene units, 100 g of coconut fatty amidopropyldimethylamine, as described in example B, were added over a period of 15 minutes. The reaction mixture was then heated to 70° C. and the temperature was maintained until the heat of reaction had passed. The mixture was then heated to 98° C. After about 7 h, the content of amide was below 0.5%. 305.6 g of an aqueous betaine solution with 48% solids were obtained which had the following composition:
Betaine content: 37.7%
Water: 52.0%
Viscosity: 180 mPa·s

Example 3.2

(Not in Accordance with the Invention)

33.2 g of monochloroacetic acid and 99.6 g of water were weighed into a 1 l four-necked flask fitted with stirrer, thermometer, reflux condenser and dropping funnel. 29.6 g of 50% strength sodium hydroxide were added via the dropping funnel with stirring. The temperature increased during this addition to about 50° C. Over a period of 15 minutes, 100 g of coconut fatty amidopropyldimethylamine, as described in example B, were added. The reaction mixture was then heated to 70° C. and the temperature was maintained until the heat of reaction had passed. In this phase, solidification or gelling took place. The reaction mixture became unstirrable. Dilution was not possible since the amount of water added was no longer stirred in. There was therefore no reaction and no formation of an aqueous betaine solution.
Betaine content: cannot be determined
Water: 45.0%
Viscosity: solid

Example 4.1

(According to the Invention)

42 g of Na monochloroacetate and 122.6 g of water were weighed into a 1 l four-necked flask fitted with stirrer, thermometer, reflux condenser and dropping funnel. Following the addition of 6.7 g of L-glutamic acid, the mixture was heated to 50° C. and maintained at this temperature for 30 minutes. Following the addition of 1.3 g of polyethoxylated castor oil having 200 oxyethylene units, 100 g of coconut fatty amidopropyldimethylamine, as described in example C, were added over a period of 15 minutes. The reaction mixture was then heated to 70° C. and the temperature was maintained until the heat of reaction had passed. The mixture was then heated to 98° C. After about 7 h, the content of amide was below 0.5%. 272.7 g of an aqueous betaine solution of the following composition were obtained:
Betaine content: 44.9%
Water: 45.0%
Viscosity: 400 mPa·s

Example 4.2

(According to the Invention)

42 g of Na monochloroacetate and 127.6 g of water were weighed into a 1 l four-necked flask fitted with stirrer, thermometer, reflux condenser and dropping funnel. Following the addition of 1.3 g of polyethoxylated castor oil having 200 oxyethylene units, 100 g of coconut fatty amidopropyldimethylamine, as described in example C, were added over a period of 15 minutes. The reaction mixture was then heated to 70° C. and the temperature was maintained until the heat of reaction had passed. Following the addition of 6.9 g of L-glutamic acid, the mixture was heated to 98° C. After about 6.5 h, the content of amide was below 0.5%. 272.4 g of an aqueous betaine solution of the following composition were obtained:
Betaine content: 41.2%
Water: 46.0%
Viscosity: 160 mPa·s

Example 5

(According to the Invention)

32.5 g of monochloroacetic acid and 106.8 g of water were weighed into a 1 l four-necked flask fitted with stirrer, thermometer, reflux condenser and dropping funnel. 28.9 g of 50% strength sodium hydroxide were added via the dropping funnel with stirring. The temperature increased during this addition to about 50° C. Over a period of 15 minutes, 100 g of coconut fatty amidopropyldimethylamine, as described in example A.1, with a content of 1.3 g of polyethoxylated glyceryl palmitate having 200 EO units were added. The reaction mixture was then heated to 70° C. and the temperature was maintained until the heat of reaction had passed. The mixture was then heated to 98° C. After about 7 h, the content of amide was below 0.5%. 269.5 g of an aqueous betaine solution of the following composition were obtained:
Betaine content: 43.9%
Water: 45.0%
Viscosity: 205 mPa·s

Example 6

(According to the Invention)

32.5 g of monochloroacetic acid and 106.8 g of water were weighed into a 1 l four-necked flask fitted with stirrer, thermometer, reflux condenser and dropping funnel. 28.9 g of 50% strength sodium hydroxide were added via the dropping funnel with stirring. The temperature increased during this addition to about 50° C. Over a period of 15 minutes, 100 g of coconut fatty amidopropyldimethylamine, as described in example A.1, with a content of 1.3 g of polyethoxylated sorbitan laurate having 160 EO units were added. The reaction mixture was then heated to 70° C. and the temperature was maintained until the heat of reaction had passed.

The mixture was then heated to 98° C. After about 7 h, the content of amide was below 0.5%. 269.5 g of an aqueous betaine solution of the following composition were obtained:
Betaine content: 43.7%
Water: 45.0%
Viscosity: 210 mPa·s

Example 7

(According to the Invention)

32.5 g of monochloroacetic acid and 106.8 g of water were weighed into a 1 l four-necked flask fitted with stirrer, thermometer, reflux condenser and dropping funnel. 28.9 g of 50% strength sodium hydroxide were added via the dropping funnel with stirring. The temperature increased during this addition to about 50° C. Over a period of 15 minutes, 100 g of coconut fatty amidopropyldimethylamine, as described in example A.1, with a content of 1.3 g of polyethoxylated coconut fat having 200 EO units were added. The reaction mixture was then heated to 70° C. and the temperature was maintained until the heat of reaction had passed.

The mixture was then heated to 98° C. After about 7 h, the content of amide was below 0.5%. 269.5 g of an aqueous betaine solution of the following composition were obtained:
Betaine content: 42.9%
Water: 46.0%
Viscosity: 120 mPa·s

Example 8

(According to the Invention)

42 g of Na monochloroacetate and 127.6 g of water were weighed into a 1 l four-necked flask fitted with stirrer, thermometer, reflux condenser and dropping funnel. Following the addition of 1.3 g of polyethoxylated castor oil having 200 oxyethylene units, 100 g of coconut fatty amidopropyldimethylamine, as described in example C, were added over a period of 15 minutes. The reaction mixture was then heated to 70° C. and the temperature was maintained until the heat of reaction had passed. Following the addition of 15 g of citric acid, the mixture was heated to 98° C. After about 6.5 h, the content of amide was below 0.5%. 272.4 g of an aqueous betaine solution of the following composition were obtained:
Betaine content: 44.2%
Water: 45.0%
Viscosity: 120 mPa·s

Application Example A

Concentrated Dishwashing Detergents

|  | Composition in % by wt. | | | | | | |
| --- | --- | --- | --- | --- | --- | --- | --- |
|  | A1 | A2 | A3 | A4 | A5 | A6 | A7 |
| Na $C_{12-14}$ fatty alcohol 2EO sulfate | 16 | 16 | 16 | 16 | 2 | 10 | 24 |
| Sec. Na $C_{12-16}$-alkanesulfonate | 8 | 8 | 8 | 8 | — | 20 | — |
| Na/Mg $C_{12}$-alkylbenzenesulfonate | — | — | — | — | 6 | — | — |
| Cocamidoalkylbetaine (according to the invention) | 8 | 8 | 8 | 2 | 2 | — | 2 |
| Cocoamphomonoacetate | 1 | 2 | — | 8 | — | 2 | 2 |
| Dimethylcocoalkylamine oxide | — | — | — | — | — | — | 2 |
| Citric acid polyethoxy lauryl ether sulfosuccinate disodium salt | — | — | 2 | — | — | — | — |
| Cocoamide DEA | — | — | — | — | 2 | — | — |
| $C_{9-13}$-alcohol ethoxylate | — | — | — | — | 2.5 | — | 4 |
| PEG-80 glyceryl cocoate | — | — | — | — | 1.5 | — | — |
| Ethanol | 8 | 8 | 8 | 8 | — | 8 | 8 |
| Citric acid monohydrate | 0.2 | 0.2 | 0.2 | 0.2 | 0.1 | 0.2 | 0.2 |
| Water, perfume, dye, auxiliaries | ad 100 | ad 100 | ad 100 | ad 100 | ad 100 | ad 100 | ad 100 |

|  | Composition in % by wt. | | | | | | |
| --- | --- | --- | --- | --- | --- | --- | --- |
|  | A8 | A9 | A10 | A11 | A12 | A13 | A14 |
| Mg $C_{12-14}$ fatty alcohol EO sulfate | — | — | — | 13 | — | 20 | 16 |
| Na $C_{12-14}$ fatty alcohol EO sulfate | 14 | 5 | 27.5 | 15 | 22 | 10 | — |
| Na/Mg $C_{12}$-alkylbenzenesulfonate | — | 15 | — | — | — | — | — |
| Sec. Na $C_{12-16}$-alkanesulfonate | — | — | — | — | 11 | — | 8 |
| Cocamidoalkylbetaine (according to the invention) | 3 | 5 | 2.5 | 2 | 11 | 3 | 7.6 |
| $C_{8-10}$-alkyl polyglucoside | 4 | — | 2.5 | 8 | — | — | — |
| Dimethylcocoalkylamine oxide | — | — | — | 1.5 | — | — | — |
| N-methyl-fatty acid glucamide | — | — | — | 1.3 | — | — | — |
| $C_{9-13}$-alcohol pentaethoxylate | — | — | — | — | — | — | — |
| $C_{10-14}$-alcohol alkoxylate | — | — | — | 4.5 | — | — | — |
| $C_{12-18}$-alcohol heptaethoxylate | — | 2 | — | — | — | — | — |
| $C_{12-16}$-alcohol pentaethoxylate | — | — | — | — | 5 | 0.5 | — |
| Na/$NH_4$-cumenesulfonate | — | — | — | — | — | — | — |
| Ethanol | 6 | 6 | 8 | 6.5 | 8 | 8 | 5 |
| Citric acid monohydrate | 0.2 | 0.2 | 0.2 | 0.2 | 0.2 | 0.2 | 0.2 |
| Water, perfume, dye, auxiliaries | ad 100 | ad 100 | ad 100 | ad 100 | ad 100 | ad 100 | ad 100 |

Reduction in the Alcohol Content as a Result of the Cocoamidoalkylbetaine Prepared According to the Invention Variously Prepared Betaines in Formulation A14

| Composition CAPB* in A14 | Viscosity 4% EtOH | Viscosity 5% EtOH | Viscosity 6% EtOH |
|---|---|---|---|
| Market product Tego ® betaine F50 | | 800 | 460 |
| Ex. 1.4 | 860 | 450 | |
| Ex. 4.1 | | 530 | |
| Ex. 1.1 | | 410 | |
| Ex. 1.2 | | 440 | |
| Ex. 4.2 | | 420 | |

*Cocoamidopropylbetaine

In standard commercial dishwashing detergent formulations, ≧5% by weight of ethanol were usually required in order to make and keep the formulation flowable. As can be seen from the table, as a result of the cocoamidoalkylbetaine according to the invention, about 20% of the required alcohol can be saved.

In examples A1 to A13, comparable results were obtained.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A process for the preparation of highly concentrated flowable and pumpable aqueous solutions of betaines of the general formula (III)

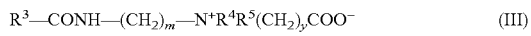

$$R^3\text{—CONH—}(CH_2)_m\text{—}N^+R^4R^5(CH_2)_y COO^- \quad (III)$$

in which $R^3$ is an alkyl radical of a fatty acid, $R^4$, $R^5$ are identical or different alkyl radicals having 1 to 4 carbon atoms, m may be 1 to 3 and y may be 1, 2, 3, with a betaine content of at least 32% by weight comprising:

quaternizing compounds containing tertiary amine nitrogen with ω-halocarboxylic acids, wherein 0.1 to less than 3% by weight, based on the betaine end product, of one or more micellar thickeners having a HLB value of greater than 12 are added to the reaction mixture before or during the quaternization reaction.

2. The process as claimed in claim 1, wherein from about 0.1 to about 1% by weight, based on the betaine end product, of said at least one or more micellar thickeners is added.

3. The process as claimed in claim 1, wherein said one or more micellar thickeners comprise a nonionic surfactant.

4. The process as claimed in claim 1, wherein said one or more micellar thickeners comprise a polyoxyetylene ether, esters of a hydroxy fatty acid or of a hydroxy fatty acid glycerides or mixtures thereof.

5. The process as claimed in claim 1, further comprising at least one compound selected from the group consisting of sulfobetaines, amphoglycinates, trimethylglycine, amino acids, N-betaines based on amino acids, monocarboxamides, monocarboxamidoamines, dicarboxylic monoamides, dicarboxylic diamides, polycarboxylic monoamides, polycarboxylic diamides, monobasic carboxylic acids which are optionally hydroxyl-functionalized, difunctional carboxylic acids, polyfunctional carboxylic acids, water-soluble carbohydrates, and polyols.

6. The process as claimed in claim 1, further comprising an amidation step that occurs prior to said quaternizing step, wherein the amidation step is carried out in the presence of at least one monobasic carboxylic acid or polybasic carboxylic acid.

* * * * *